US 6,523,568 B1

(12) United States Patent
Trantham

(10) Patent No.: US 6,523,568 B1
(45) Date of Patent: Feb. 25, 2003

(54) COMBINATION AIR VENT/PROBE PORT AND METHOD OF CONSTRUCTING SAME

(75) Inventor: John M. Trantham, Hurst, TX (US)

(73) Assignee: Flow Design, Inc., Dallas, TX (US)

( * ) Notice: Subject to any disclaimer, the term of this patent is extended or adjusted under 35 U.S.C. 154(b) by 124 days.

(21) Appl. No.: 09/823,605

(22) Filed: Mar. 30, 2001

(51) Int. Cl.$^7$ .............................................. F16K 11/02
(52) U.S. Cl. .................. 137/599.16; 251/344; 251/345; 251/149.1
(58) Field of Search ................................ 251/343, 345, 251/149.1, 344; 137/599.16

(56) References Cited

U.S. PATENT DOCUMENTS

| | | | | |
|---|---|---|---|---|
| 4,265,428 A | * | 5/1981 | Rosemeier et al. | 251/346 |
| 4,541,456 A | * | 9/1985 | Troy | 251/346 X |
| 4,915,356 A | * | 4/1990 | Guild et al. | 251/346 X |
| 4,926,704 A | * | 5/1990 | Survil et al. | 73/756 |
| 5,342,316 A | * | 8/1994 | Wallace | 251/149.1 X |

* cited by examiner

*Primary Examiner*—Kevin Lee
(74) *Attorney, Agent, or Firm*—Baker Botts L.L.P.

(57) ABSTRACT

According to one embodiment of the invention, a combination air vent/probe port includes an outer body adapted to couple to a conduit, the outer body formed with a longitudinal bore defining an inner wall, the longitudinal bore having a seating surface. The combination air vent/probe port also includes an inner sleeve adapted to adjustably engage the outer body, the inner sleeve having an outer diameter and formed with an inner chamber. Furthermore, a resilient member is disposed within the inner chamber, the resilient member operable to allow a probe to be inserted therethrough when the inner sleeve is adjustably engaged with the outer body and an end of the inner sleeve is engaged with the seating surface. The inner sleeve, when adjustably engaged with the outer body, is axially movable with respect to the outer body such that when the end of the inner sleeve is not engaged with the seating surface a flow passage is produced between the outer diameter and the inner wall, the flow passage operable to allow fluid media to escape from the conduit.

31 Claims, 3 Drawing Sheets

COMBINATION AIR VENT/PROBE PORT AND METHOD OF CONSTRUCTING SAME

TECHNICAL FIELD OF THE INVENTION

This invention relates generally to the field of piping systems and, more specifically, to a combination air vent/probe port and method of constructing same.

BACKGROUND OF THE INVENTION

Piping systems are used for many applications. One such application is the transportation of fluid. Most often, piping systems that transport fluid require that various characteristics of the fluid, such as pressure and temperature, be measured. Typically, a fitting (sometimes referred to as a port) is radially attached to a pipe in the piping system so that a probe can be inserted therethrough such that a tip of the probe contacts the fluid to be measured.

In addition, some piping systems require that air within the piping system be vented off to atmosphere. Typically, this requires an additional fitting located on a pipe in the piping system so that any air within the piping system can be vented to atmosphere. These "air vents" inevitably allow both air and water to escape in a non-controlled manner. This means that any fluid inside the piping system leaks out onto the pipes, which can cause corrosion and/or other harmful effects.

SUMMARY OF THE INVENTION

The challenges in the field of piping systems continue to increase with demands for more and better techniques having greater flexibility and adaptability. Therefore, a need has arisen for a new combination air vent/probe port and method of constructing same.

In accordance with the present invention, a combination air vent/probe port and method of constructing same is provided that addresses disadvantages and problems associated with previously developed apparatuses and methods.

According to one embodiment of the invention, a combination air vent/probe port includes an outer body adapted to couple to a conduit, the outer body formed with a longitudinal bore defining an inner wall, the longitudinal bore having a seating surface. The combination air vent/probe port also includes an inner sleeve adapted to adjustably engage the outer body, the inner sleeve having an outer diameter and formed with an inner chamber. Furthermore, a resilient member is disposed within the inner chamber, the resilient member operable to allow a probe to be inserted therethrough when the inner sleeve is adjustably engaged with the outer body and an end of the inner sleeve is engaged with the seating surface. The inner sleeve, when adjustably engaged with the outer body, is axially movable with respect to the outer body such that when the end of the inner sleeve is not engaged with the seating surface a flow passage is produced between the outer diameter and the inner wall, the flow passage operable to allow fluid media to escape from the conduit.

Certain embodiments of the invention provide various technical advantages. For example, in one embodiment, only one piping apparatus is required that functions both as an air vent as well as a pressure/temperature test port. This "combination" piping apparatus eliminates the need for two separate piping apparatuses to handle both functions, thereby saving considerable time and expense as well as reducing the number of discontinuities in a piping system. In an embodiment of the invention where the piping apparatus is being used as an air vent, a hose can be attached to the apparatus to properly dispose of any liquid, thereby preventing any liquid from spilling onto the pipe and surrounding areas.

Other technical advantages are readily apparent to one skilled in the art from the following figures, descriptions, and claims.

BRIEF DESCRIPTION OF THE DRAWINGS

For a more complete understanding of the invention, and for further features and advantages, reference is now made to the following description, taken in conjunction with the accompanying drawings, in which.

DETAILED DESCRIPTION OF EXAMPLE EMBODIMENTS OF THE INVENTION

Example embodiments of the present invention and their advantages are best understood by referring now to FIGS. 1–5 of the drawings, in which like numerals refer to like parts.

Figure 1:
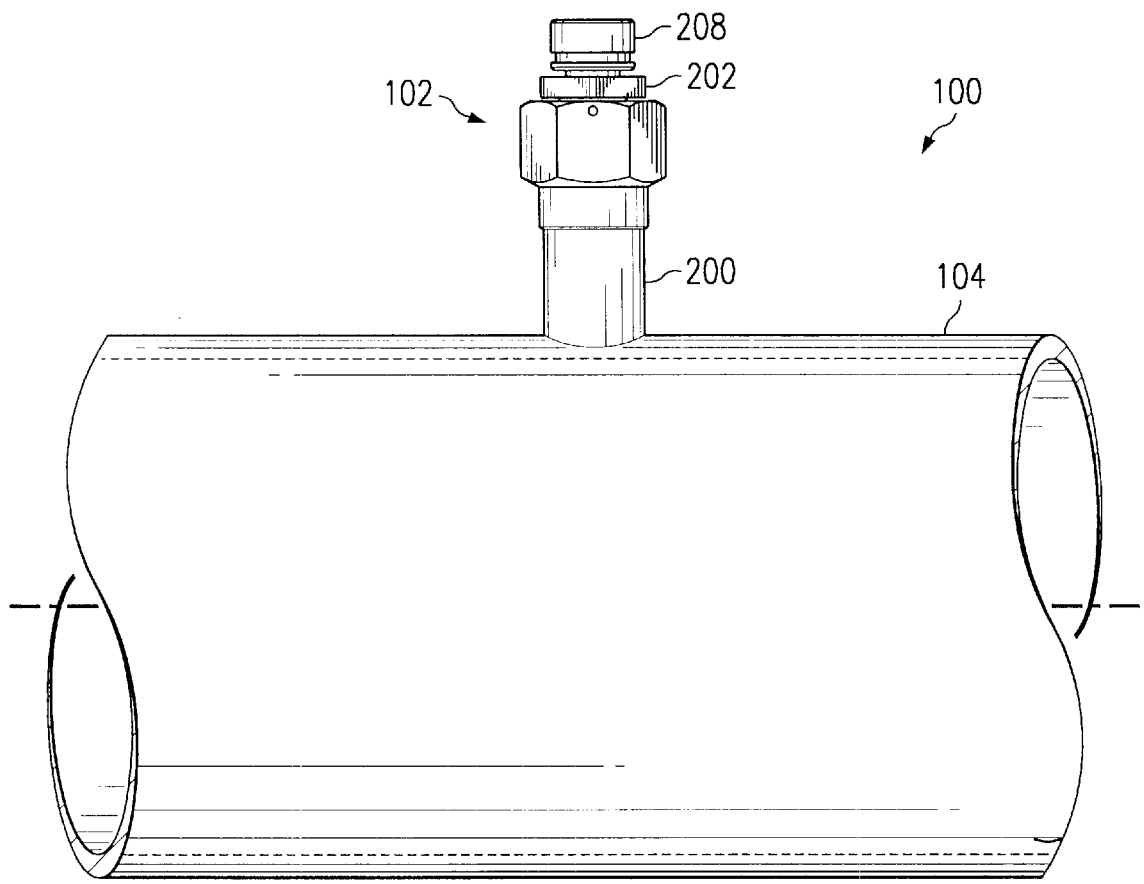
FIG. 1 is an elevation view illustrating a piping apparatus coupled to a pipe according to one embodiment of the present invention.

FIG. 1 is an elevation view illustrating a piping system 100 utilizing a piping apparatus 102 coupled to a pipe 104 in accordance with one embodiment of the present invention. Piping system 100 may be any conventional piping system, such as that used in an HVAC system, and apparatus 102 may be coupled to pipe 104 in any conventional manner, such as welding, brazing, or through a screwed connection. In one mode of operation, apparatus 102 functions as an air vent. In another mode of operation, apparatus 102 functions as a probe port. Apparatus 102 combines these two functions into one device, thereby saving considerable expense and reducing the number of fittings and/or discontinuities in piping system 100. The reduction of the number of discontinuities in piping system 100 reduces turbulence, which increases the efficiency of piping system 100. Details of apparatus 102 are described below in conjunction with FIGS. 2 and 3, followed by a description of apparatus 102 functioning as a probe port in FIG. 4 and a description of apparatus 102 functioning as an air vent in FIG. 5.

Figure 3:
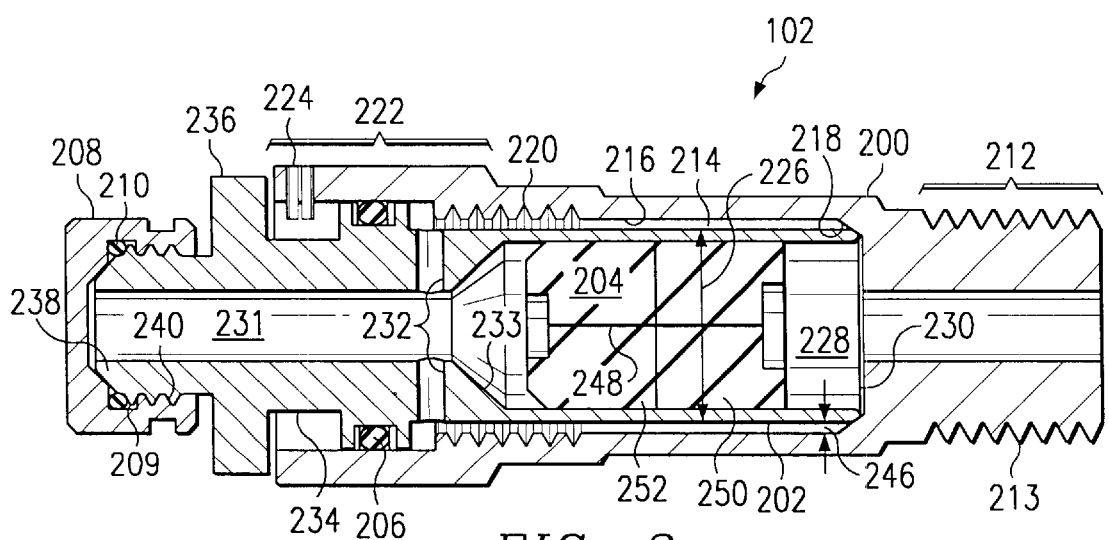
FIG. 3 is a cross-sectional view of the piping apparatus of FIG. 1.
Figure 2:
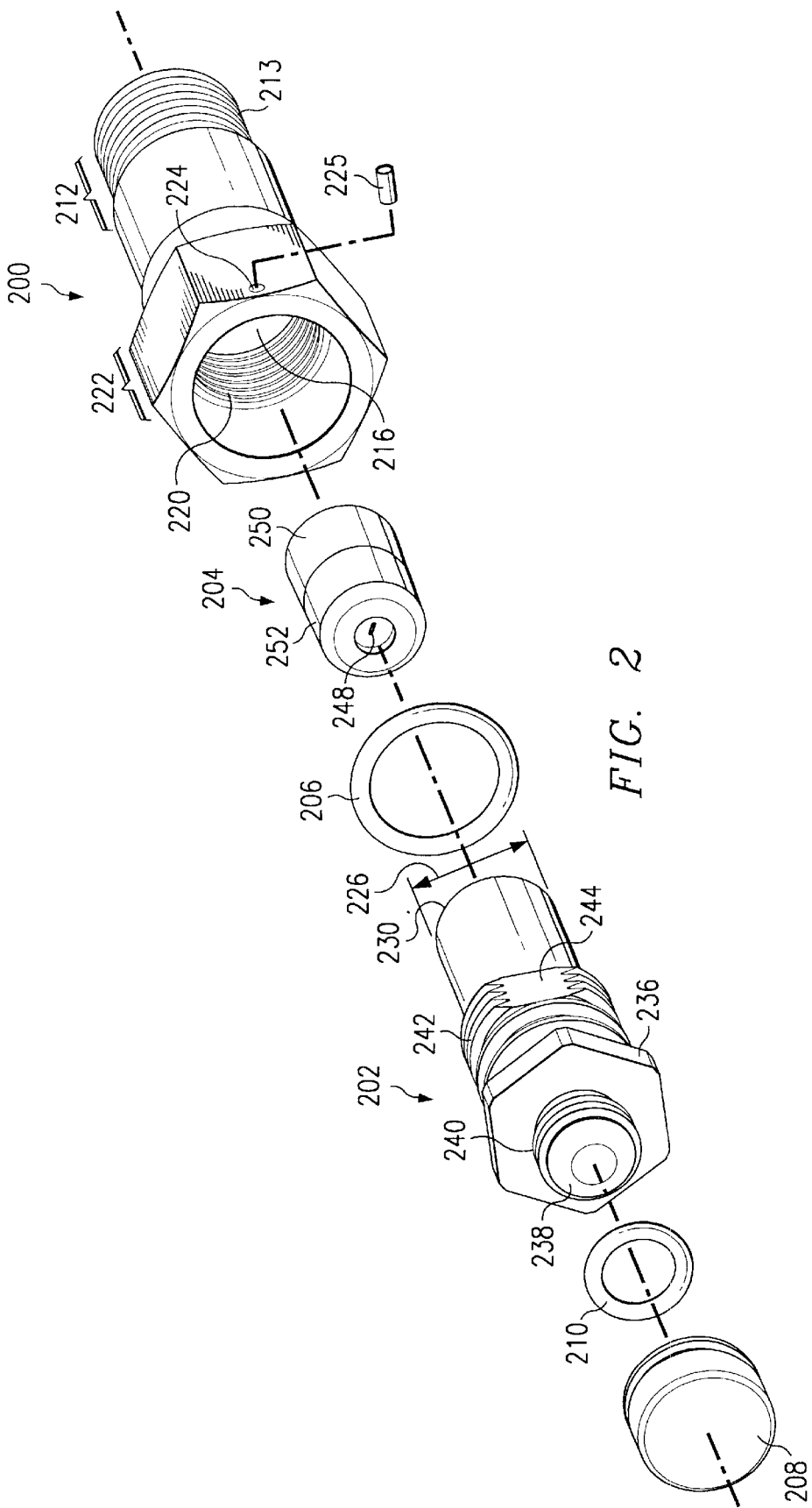
FIG. 2 is a perspective view of the piping apparatus of FIG. 1.

FIG. 2 is an exploded, perspective view of apparatus 102, and FIG. 3 is an assembled cross-sectional view of apparatus 102. Apparatus 102 includes an outer body 200, an inner sleeve 202, a resilient member 204, and an O-ring 206. Apparatus 102 may also include a cap 208 and a cap O-ring 210.

Outer body 200, in one embodiment, is formed from brass; however, outer body 200 may be formed from other suitable materials, such as stainless steel, plastic, or composite material. In the illustrated embodiment, outer body 200 includes an end 212 that is adapted to couple to pipe 104. In one embodiment, end 212 mechanically couples to pipe 104 via threads 213; however, end 212 may couple to pipe 104 in other suitable manners, such as welding or brazing. To facilitate coupling of outer body 200 to pipe 104, outer body 200 may include a hex head section 222. Other suitable methods for facilitating the coupling of outer body 200 to pipe 104 may be utilized.

Outer body 200 is formed with a longitudinal bore 214 (FIG. 3) that defines an inner wall 216 and a seating surface 218 (FIG. 3). Longitudinal bore 214, in one embodiment, is substantially cylindrical. However, longitudinal bore 214 may be other suitable shapes. Longitudinal bore 214 is adapted to accept inner sleeve 202, as illustrated in FIG. 3. To facilitate the acceptance of inner sleeve 202, inner wall 216, in one embodiment, is formed with suitable female threads 220.

Seating surface 218 (near end 212) provides a seating surface for inner sleeve 202 when apparatus 102 is being utilized as a probe port, which is described below in conjunction with FIG. 4.

Outer body 200 may also include an aperture 224 formed therein that is adapted to accept a pin 225 (FIG. 2) that prevents inner sleeve 202 from decoupling from outer body 200. Aperture 224 and pin 225 are any suitable shape and size, and pin 225 is formed from any suitable material. Other suitable methods may be utilized to prevent inner sleeve 202 from decoupling from outer body 200, such as providing a "roll-over crimp" in outer body 200.

In the illustrated embodiment, inner sleeve 202 has an outer diameter 226, an inner chamber 228, an end 230, at least one radial bore 232 (FIG. 3), an indented section 234 (FIG. 3), a hex head section 236, and a distal end 238 having threads 240. Inner sleeve 202 is adapted to adjustably engage outer body 200. In one embodiment, this adjustable engagement is accomplished via male threads 242 having at least one flat region 244 as shown best in FIG. 2. Inner sleeve 202 may be formed from brass or other suitable materials, such as stainless steel, plastic, or composite material.

Outer diameter 226 is typically less than the diameter of inner wall 216 of outer body 200 such that when inner sleeve 202 is adjustably engaged with outer body 200 a gap is created between outer diameter 226 and inner wall 216 as denoted by arrows 246 in FIG. 3. The function of gap 246 is described below in conjunction with FIG. 5.

Inner chamber 228, in one embodiment, is cylindrical; however, inner chamber 228 may be formed in other suitable shapes. Inner chamber 228 houses resilient member 204, which is described in more detail below. In the illustrated embodiment, inner chamber 228 is formed with a first chamber section 229 that tapers down to a second chamber section 231, which results in a tapered surface 233 that acts as a stop for resilient member 204 so that resilient member 204 retains its position within first chamber section 229.

Figure 4:
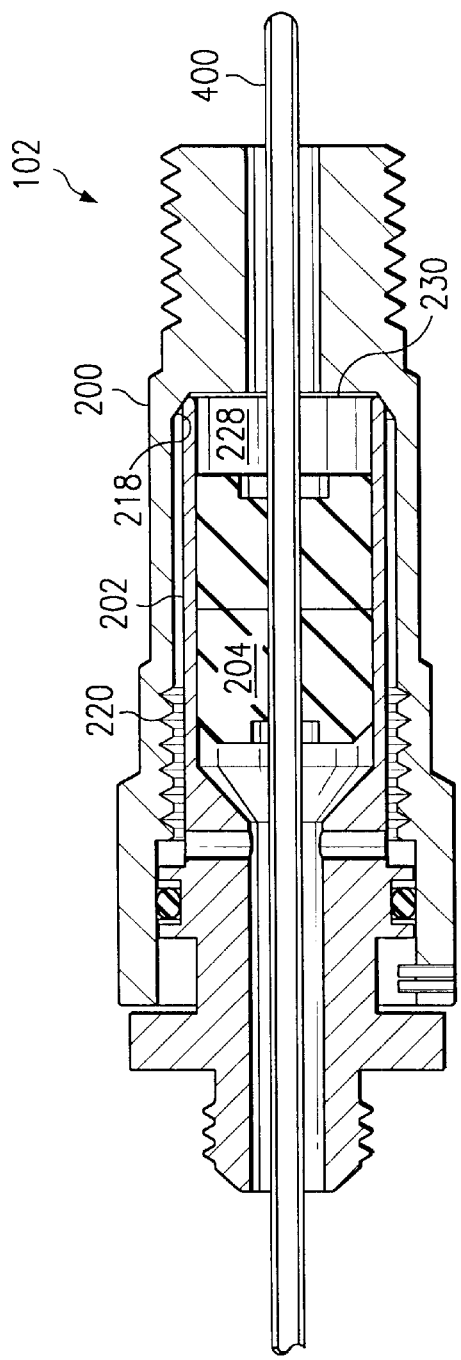
FIG. 4 is the cross-sectional view of FIG. 3 showing a test probe inserted therethrough.

End 230 seats against seating surface 218 to prevent fluid media in pipe 104 from entering gap 246 when apparatus 102 is either not being used at all or being used as a probe port, as discussed in FIG. 4. When end 230 is not seated against seating surface 218, then fluid media from pipe 104 is allowed to enter gap 246 when apparatus 102 is being used as an air vent, as discussed more fully below in conjunction with FIG. 5.

Radial bore 232 couples gap 246 with second chamber section 231. Inner sleeve 202 may be formed with one or any number of radial bores 232, and radial bores 232 may be any desired shape. Radial bore 232 allows fluid media in gap 246 to enter first chamber section 231 when apparatus 102 is being used as an air vent, as discussed more fully below in conjunction with FIG. 5.

Any suitable method may be used for facilitating the adjustable engagement of inner sleeve 202 with outer body 200. However, in the illustrated embodiment, hex head section 236 facilitates the threaded engagement of inner sleeve 202 to outer body 200.

Figure 5:
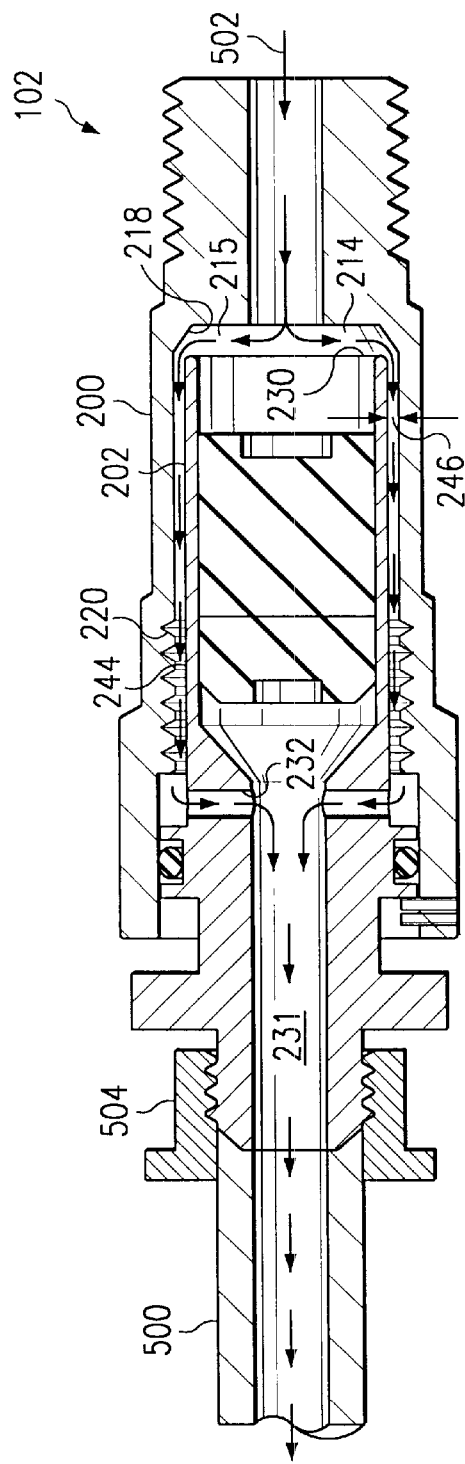
FIG. 5 is the cross-sectional view of FIG. 3 showing the piping apparatus being used as an air vent.

Distal end 238 has any suitable threads 240 that are adapted to couple to either cap 208 or a hose 500 (FIG. 5).

In the illustrated embodiment, resilient member 204 has a slit 248 formed therein that is operable to allow a probe 400 (FIG. 4) to be inserted therethrough when apparatus 102 is being utilized as a probe port. The size and shape of slit 248 depends on the size and shape of probe 400. Resilient member 204 may be formed from any suitable material that allows slit 248 to seal around probe 400, such as neoprene or EPDM. In addition, resilient member 204 may be a single durometer or a dual durometer resilient member. In a particular embodiment, resilient member 204 has a first portion 250 having a hardness of between 25 and 45 durometer and a 30 second portion 252 having a hardness of between 60 and 80 durometer. Other embodiments of resilient member 204 are described in U.S. Pat. No. 4,926,704, which is herein incorporated by reference. The utilization of resilient member 204 is described further below in conjunction with FIG. 4. O-ring 206 is any suitable o-ring that provides a seal between inner sleeve 202 and outer body 200 as illustrated best in FIG. 3. O-ring 206 may be formed from any suitable material depending on the operating conditions for piping system 100. O-ring 206 functions to prevent fluid media from seeping between inner sleeve 202 and outer body 200 and to direct fluid media to the appropriate flow passages as described more fully below in conjunction with FIG. 5.

Cap 208 and cap O-ring 210 cooperate to prevent any unexpected leakage of fluid media from pipe 104 when apparatus 102 is not being used as either a probe port or an air vent. Cap 208 is formed from any suitable material, such as brass, and has threads 209 that are adapted to couple to threads 240 of distal end 238. Cap O-ring 210 is formed from any suitable material.

According to the teachings of the present invention, when end 230 of inner sleeve 202 is engaged with seating surface 218, then resilient member 204 is operable to allow a probe to be inserted therethrough so that apparatus 102 functions as a probe port. Conversely, when end 230 of inner sleeve 202 is not engaged with seating surface 218 of outer body 200, gap 246 acts as a flow passage between outer diameter 226 and inner wall 216 such that fluid media escapes from pipe 104. Details of a probe port mode of operation are described below in conjunction with FIG. 4, and details of an air vent mode of operation are described below in conjunction with FIG. 5.

FIG. 4 is a cross-sectional view of apparatus 102 showing apparatus 102 utilized as a probe port. For apparatus 102 to function as a probe port, inner sleeve 202 is adjustably engaged (e.g., threadedly engaged via female threads 220 and male threads 242) with outer body 200 such that end 230 of inner sleeve 202 engages seating surface 218 of outer body 200. In this way, any fluid media within pipe 104 is not able to escape because of resilient member 204 being disposed in inner chamber 228. Accordingly, probe 400 is inserted into slit 248 of resilient member 204 as illustrated. Probe 400 may be any suitable test probe, such as a pressure or temperature test probe well known in the art of piping systems.

FIG. 5 is a cross-sectional view of apparatus 102 being utilized as an air vent. In this embodiment, inner sleeve 202 is adjustably engaged (e.g., threadedly engaged via female threads 220 and male threads 242) with outer body 200 such that end 230 of inner sleeve 202 is not engaged with seating surface 218 of outer body 200. This non-engagement produces a flow passage as illustrated by arrows 502. The flow passage includes a portion 215 of longitudinal bore 214, gap 246, radial bore 232, and second chamber section 231. In an embodiment where inner sleeve 202 is threadedly engaged with outer body 200, male threads 242 are discontinuous around outer diameter 226 of inner sleeve 202, thereby producing flat regions 244 (as shown best in FIG. 2) that allow the fluid media to flow from gap 246 to radial bores 232. Male threads 242 may have one or any number of flat regions 244.

Accordingly, fluid media, which may be air, water, or other suitable fluid media travels in the flow passage and out through hose 500 as illustrated. Hose 500 may be any suitable hose to draw fluid media from pipe 104 in a controlled manner. Hose 500 prevents any fluid media, such as water, from escaping apparatus 102 and dripping on pipe 104 of piping system 100, and is coupled to inner sleeve 202 in any suitable manner, such as by a fitting 504 that is adapted to couple to threads 240 of distal end 238.

Although example embodiments of the invention and their advantages are described in detail, a person skilled in the art could make various alternations, additions, and omissions without departing from the spirit and scope of the present invention as defined by the appended claims.

What is claimed is:

1. A piping apparatus, comprising:
    an outer body adapted to couple to a conduit, the outer body formed with a longitudinal bore defining an inner wall, the longitudinal bore having a seating surface;
    an inner sleeve adapted to threadedly engage the outer body, the inner sleeve having an outer diameter and formed with an inner chamber;
    a resilient member disposed within the inner chamber, the resilient member operable to allow a probe to be inserted therethrough when the inner sleeve is threadedly engaged with the outer body and a first end of the inner sleeve is engaged with the seating surface; and
    wherein the inner sleeve, when threadedly engaged with the outer body, is axially movable with respect to the outer body such that when the first end of the inner sleeve is not engaged with the seating surface a flow passage is produced between the outer diameter and the inner wall, the flow passage operable to allow fluid media to escape from the conduit.

2. The apparatus of claim 1, wherein the longitudinal bore is substantially cylindrical.

3. The apparatus of claim 1, wherein the inner chamber is formed with a first chamber section that tapers down to a second chamber section, and wherein the resilient member is disposed within the first chamber section.

4. The apparatus of claim 3, further comprising a radial bore coupling the flow passage to the second chamber section, whereby the flow passage is operable to allow fluid media to escape from the conduit through the radial bore and out of the second chamber section.

5. The apparatus of claim 4, wherein the inner sleeve is formed with a threaded portion adjacent a second end, the threaded portion operable to couple to a hose.

6. The apparatus of claim 1, wherein the inner sleeve has a threaded portion formed on the outer diameter, the threaded portion discontinuous around the outer diameter.

7. The apparatus of claim 1, wherein the resilient member has a slit formed therein sized to allow the probe to be inserted through the resilient member.

8. The apparatus of claim 1, wherein the resilient member includes a first portion and a second portion, the first portion having a hardness of between 25 and 45 durometer, the second portion having a hardness of between 60and 80durometer.

9. The apparatus of claim 1, wherein the fluid media comprises air.

10. The apparatus of claim 1, wherein the fluid media comprises water.

11. The apparatus of claim 1, further comprising a seal disposed between the inner wall and the outer diameter.

12. A piping apparatus, comprising:
    an outer body adapted to couple to a conduit, the outer body formed with a substantially cylindrical longitudinal bore defining an inner wall, the longitudinal bore having a seating surface;
    an inner sleeve adapted to threadedly engage the outer body, the inner sleeve having an outer diameter and formed with a first chamber section that tapers down to a second chamber section, the inner sleeve formed with a radial bore that extends from the outer diameter to the second chamber section, the inner sleeve further formed with a threaded portion on the outer diameter, the threaded portion discontinuous around the outer diameter;
    a resilient member disposed within the first chamber section, the resilient member having a slit formed therein that is operable to allow a probe to be inserted therethrough when the inner sleeve is threadedly engaged with the outer body and a first end of the inner sleeve is engaged with the seating surface; and
    wherein the inner sleeve, when threadedly engaged with the outer body, is axially movable with respect to the outer body such that when the first end of the inner sleeve is not engaged with the seating surface a flow passage is produced between the outer diameter and the inner wall, the flow passage operable to allow fluid media to escape from the conduit through the radial bore and out of the second chamber section.

13. The apparatus of claim 12, wherein the inner sleeve is formed with a threaded portion adjacent a second end, the threaded portion operable to couple to a hose.

14. The apparatus of claim 12, wherein the resilient member includes a first portion and a second portion, the first portion having a hardness of between 25 and 45 durometer, the second portion having a hardness of between 60 and 80 durometer.

15. The apparatus of claim 12, wherein the fluid media comprises air.

16. The apparatus of claim 12, wherein the fluid media comprises water.

17. The apparatus of claim 12, further comprising a seal disposed between the inner wall and the outer diameter.

18. The apparatus of claim 12, further comprising an aperture formed in the outer body, the aperture operable to accept a pin element for restricting the axial motion of the inner sleeve.

19. A method of constructing a piping apparatus, comprising:
    providing an outer body, the outer body adapted to couple to a conduit;
    forming a substantially cylindrical longitudinal bore in the outer body, the longitudinal bore defining an inner wall, the longitudinal bore having a seating surface;
    providing an inner sleeve having an outer diameter and formed with an inner chamber;

disposing a resilient member within the inner chamber;

forming a slit in the resilient member, the slit operable to allow a probe to be inserted therethrough when a first end of the inner sleeve is engaged with the seating surface; and adjustably engaging the inner sleeve with the outer body such that when the first end of the inner sleeve is not engaged with the seating surface a flow passage is produced between the outer diameter and the inner wall, the flow passage operable to allow fluid media to escape from the conduits.

20. The method of claim 19, further comprising:

forming the inner chamber with a first chamber section that tapers down to a second chamber section; and disposing the resilient member within the first chamber section.

21. The method of claim 19, further comprising coupling the flow passage to the second chamber section with a radial bore, whereby the flow passage is operable to allow fluid media to escape from the conduit through the radial bore and out of the second chamber section.

22. The method of claim 21, further comprising providing the inner sleeve with a threaded portion adjacent a second end of the inner sleeve, the threaded portion operable to couple to a hose.

23. The method of claim 19, wherein adjustably engaging the inner sleeve with the outer body comprises threadedly engaging the inner sleeve with the outer body by providing the inner sleeve with a threaded portion on the outer diameter, the threaded portion discontinuous around the outer diameter.

24. The method of claim 19, further comprising providing the resilient member with a first portion and a second portion, the first portion having a hardness of between 25 and 45 durometer, the second portion having a hardness of between 60 and 80 durometer.

25. The method of claim 19, wherein the fluid media comprises air.

26. The method of claim 19, wherein the fluid media comprises water.

27. The method of claim 19, further comprising disposing a seal between the inner wall and the outer diameter.

28. A piping apparatus, comprising:

an outer body adapted to couple to a conduit, the outer body formed with a longitudinal bore defining an inner wall, the longitudinal bore having a seating surface;

an inner sleeve adapted to adjustably engage the outer body, the inner sleeve having an outer diameter and formed with an inner chamber;

a resilient member disposed within the inner chamber, the resilient member having a slit formed therein that is operable to allow a probe to be inserted therethrough when the inner sleeve is adjustably engaged with the outer body and a first end of the inner sleeve is engaged with the seating surface; and wherein the inner sleeve, when adjustably engaged with the outer body, is axially movable with respect to the outer body such that when the first end of the inner sleeve is not engaged with the seating surface a flow passage is produced between the outer diameter and the inner wall, the flow passage operable to allow fluid media to escape from the conduit.

29. The apparatus of claim 28, further comprising a radial bore coupling the flow passage to the second chamber section, whereby the flow passage is operable to allow fluid media to escape from the conduit through the radial bore and out of the second chamber section.

30. The apparatus of claim 28, wherein the inner sleeve is adapted to threadedly engage the outer body via a threaded portion formed on the outer diameter, the threaded portion discontinuous around the outer diameter.

31. The apparatus of claim 28, wherein the resilient member includes a first portion and a second portion, the first portion having a hardness of between 25 and 45 durometer, the second portion having a hardness of between 60 and 80 durometer.

* * * * *